(12) United States Patent
Dody et al.

(10) Patent No.: US 10,631,875 B2
(45) Date of Patent: Apr. 28, 2020

(54) HAEMOSTATIC BRACELET

(71) Applicant: FRESENIUS MEDICAL CARE DEUTSCHLAND GMBH, Bad Homburg (DE)

(72) Inventors: Cyril Dody, Sain Bel (FR); François Dumont D'Ayot, Lyons (FR); Philippe Laffay, Sainte Foy les Lyon (FR); Jacques Volle, Tassin la Demie Lune (FR)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 213 days.

(21) Appl. No.: 15/563,699

(22) PCT Filed: Apr. 1, 2016

(86) PCT No.: PCT/EP2016/057189
§ 371 (c)(1),
(2) Date: Oct. 2, 2017

(87) PCT Pub. No.: WO2016/156558
PCT Pub. Date: Oct. 6, 2016

(65) Prior Publication Data
US 2018/0070957 A1  Mar. 15, 2018

(30) Foreign Application Priority Data

Apr. 1, 2015 (FR) .................... 15 52796

(51) Int. Cl.
*A61B 17/132* (2006.01)
*A61B 17/28* (2006.01)
(Continued)

(52) U.S. Cl.
CPC ........ *A61B 17/1327* (2013.01); *A61B 17/132* (2013.01); *A61B 17/1325* (2013.01);
(Continued)

(58) Field of Classification Search
CPC .............. A61B 17/1327; A61B 17/132; A61B 17/2812; A61B 17/1325;
(Continued)

(56) References Cited

U.S. PATENT DOCUMENTS 1,957,992 A   5/1934  Cohen
2,567,182 A   9/1951  Cohen
(Continued)

FOREIGN PATENT DOCUMENTS

DE    219012 C      7/1909
EP    1 295 564 A1  3/2003
(Continued)

OTHER PUBLICATIONS

International Search Report and Written Opinion dated Jun. 13, 2016 issued in corresponding application No. PCT/EP2016/057189; in English (10 pages).
(Continued)

*Primary Examiner* — Julian W Woo
(74) *Attorney, Agent, or Firm* — Kilyk & Browersox, P.L.L.C.

(57) ABSTRACT

The invention relates to a haemostatic bracelet (1) comprising: —a clamp comprising two branches (11, 12) and a first strut (13), each branch (11, 12) being connected by one of its ends to the other branch by means of the first strut (13), —a compression element (24) placed, when the bracelet is ready for use, inside the space defined by the branches (11, 12) and the first strut (13) of the clamp or inside a projection of this space, the compression element (24) protruding in the direction of the opening between the ends of the branches (11, 12) of the clamp opposite to the first strut (13), —actuation elements (30, 40) fixed to the branches (11, 12) of the clamp so that the ends of the branches (11, 12) of the clamp
(Continued)

Figure 2A:
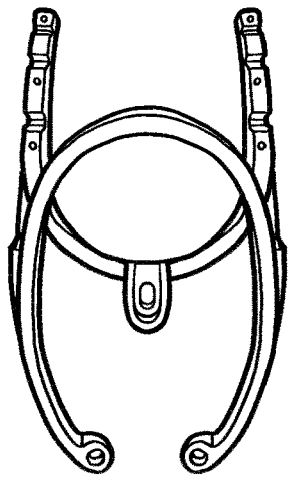

opposite to the first strut (13) can be spread by moving the ends of the actuation elements towards each other.

18 Claims, 5 Drawing Sheets

(51) Int. Cl.
  *A44C 5/00* (2006.01)
  *A61B 17/12* (2006.01)
  *A61F 13/00* (2006.01)

(52) U.S. Cl.
  CPC ........ *A61B 17/2812* (2013.01); *A44C 5/0023* (2013.01); *A61B 2017/12004* (2013.01); *A61F 2013/00468* (2013.01)

(58) Field of Classification Search
  CPC . A61B 2017/12004; A61F 2013/00468; A44C 5/0023
  See application file for complete search history.

(56) References Cited

U.S. PATENT DOCUMENTS

| | | | | |
|---|---|---|---|---|
| 3,616,497 | A * | 11/1971 | Esposito, Jr. | ......... H01L 23/291 24/542 |
| 3,802,437 | A * | 4/1974 | Kees, Jr. | ............ A61B 17/1227 606/142 |
| 4,223,673 | A | 9/1980 | Harris | |
| 4,835,824 | A * | 6/1989 | Durham | .................. A61B 17/12 24/339 |
| D340,113 | S * | 10/1993 | Knoblauch | .................. D24/143 |
| 6,638,295 | B1 | 10/2003 | Schroer | |
| 8,764,774 | B2 * | 7/2014 | Sigmon, Jr. | .......... A61B 17/122 24/535 |
| 9,107,671 | B2 * | 8/2015 | Guillot | ............... A61B 17/1327 |
| 10,172,624 | B2 * | 1/2019 | Adams | ................. A61B 17/122 |
| 2003/0055453 | A1 | 3/2003 | Akerfeldt | |

FOREIGN PATENT DOCUMENTS

| | | |
|---|---|---|
| JP | S5968544 U | 5/1984 |
| KR | 10-1435135 B1 | 8/2014 |

OTHER PUBLICATIONS

Notice of Reasons for Refusal (Office Action) for Japanese Patent Application No. 2017-547149 issued by the Japan Patent Office (JPO), dispatch dated Jan. 21, 2020, including English-language translation, 6 pages.

* cited by examiner

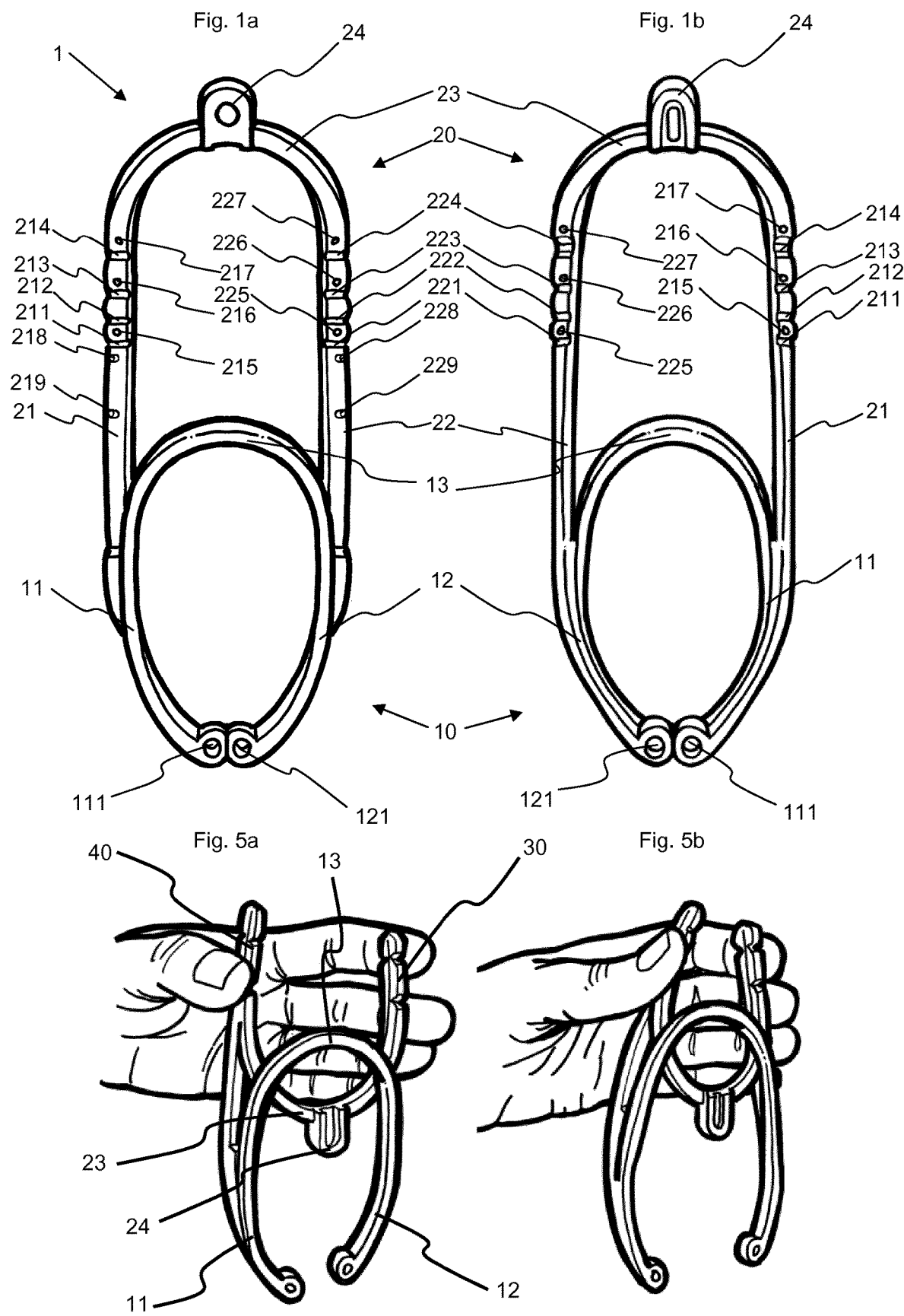

HAEMOSTATIC BRACELET

The invention relates to a haemostatic bracelet.

Haemostatic devices are frequently used for stopping bleeding following for example the disconnection of arteriovenous fistulas (AVFs) at the end of haemodialysis. When the needle is extracted, bleeding occurs that it is necessary to staunch in order to prevent a haemorrhagic risk.

The simplest method consists of applying a compress on the puncture point and exerting finger pressure on the compress. Such finger compression is a simple and economical solution and can be practised by the patient himself if he is physically capable thereof. The renal insufficiencies from which dialysis patients suffer delays haemostasis, so that the compression must last for around 10 minutes. If the patient is not in a position to provide this compression, it is usually necessary to use haemostatic devices, in order to release the medical personnel for more technical tasks.

Among haemostatic devices, haemostatic dressings, haemostatic clamps and haemostatic bracelets are known.

Haemostatic dressings are used in addition to compression. They contain agents that promote haemostasis. They do however have the drawback of being expensive.

Compression aids have been developed for replacing finger compression. Haemostatic clamps are provided with a first branch intended to bear on the rear face of the arm of the patient and a second branch, able to move with respect to the first, intended to come to bear on the compress. A spring tends to return the second branch towards the first. These clamps are in general reusable and must therefore be cleaned and sterilised between two uses. Because of the return spring, they apply a different pressure according to the diameter of the arm of the patient. The thicker the arm, the more open is the clamp and the greater the return force exerted by the spring. The pressure exerted by the clamp on the puncture point is therefore greater, the thicker the arm of the patient. The pressure of the clamp therefore depends not on the needs of the patient, but on his corpulence. Another solution consists of using a haemostatic bracelet. This is an adjustable bracelet provided with a compressing element that is placed on the compress. The bracelet is then tightened until the compressing element exerts sufficient pressure on the puncture point. The simplest bracelets are similar to a tourniquet. Upon tightening of the bracelet, often a displacement thereof is observed and therefore of the compressing point. It is therefore difficult to apply it.

The objective of the invention is to develop a haemostatic device that does not have the drawbacks mentioned above. It must in particular be able to be easy to place without risk of displacement during fitting, to adapt to the diameter of the arm of the patient and to be manufactured at low cost to allow single use.

The first objective is achieved by means of a haemostatic bracelet comprising the following elements:
- a clamp comprising two branches and a first strut, each branch being connected by one of its ends to the other branch by means of the first strut,
- a compression element placed, when the bracelet is ready for use, inside the space defined by the branches and the first strut of the clamp or inside a projection of this space, the compression element protruding in the direction of the opening between the ends of the branches of the clamp opposite to the first strut,
- actuation elements fixed to the branches of the clamp so that the ends of the branches of the clamp opposite to the first strut can be spread by moving the ends of the actuation elements towards each other.

It is preferable for the bracelet to comprise an arch provided with two branches and a second strut. Each branch is connected by its first end to the other branch by means of the second strut and by its second end to a different branch of the clamp so that, at the junction between the arch and the clamp, the branches of the arch diverge from the clamp while moving away from the end of the branches of the clamp opposite to the first strut. In addition, each branch of the arch is provided with a first articulation, the first articulations being situated facing each other and forming a first set of articulations. The compression element is placed on the second strut so as to protrude from the second strut in the opposite direction to the first articulations. The part of the arch situated between the two articulations of the first set of articulations and comprising the second strut can be folded in the direction of the clamp by pivoting about the first articulations so that the compression element can be placed inside the space defined by the branches and the first strut of the clamp or inside a projection of this space while projecting in the direction of the opening between the ends of the branches of the clamp opposite to the first strut. This configuration makes it possible to manufacture an element stored flat during storage and then to fold it at the time of use.

So that the bracelet can be adjusted to the dimensions of the arm of the patient, provision is made for providing each branch of the arch with one or more supplementary articulations, each supplementary articulation of the first branch facing a corresponding supplementary articulation of the second branch and forming with this corresponding articulation a set of supplementary articulations. The part of the arch comprising the second strut can be folded in the direction of the clamp by pivoting as required about the first set of articulations or one of the sets of supplementary articulations. The sets of supplementary articulations are further away from the junction between the arch and the clamp than the first set of articulations, so that, in the folded position of the second strut on the clamp, the compression element is closer to the opening situated between the ends of the branches of the clamp opposite to the first strut, when the second strut has pivoted about the first set of articulations, than when it has pivoted about a set of supplementary articulations.

In a favoured embodiment of the haemostatic bracelet of the invention, each branch comprises a first supplementary articulation and a second supplementary articulation, the first set of supplementary articulations being further away from the junction between the arch and the clamp than the first set of articulations and the second set of supplementary articulations being further away from the junction between the arch and the clamp than the first set of supplementary articulations.

So that the bracelet remains in its position of use with the second strut folded against the clamp, it is preferable to provide retaining means. These retaining means may consist of pins and holes. For example, one of the branches of the arch at least is provided with at least one pin and as many holes as it has articulations, the hole or holes being sized so as to receive and retain by friction the pin or one of the pins, the pin or pins being placed on the part of the branch or branches situated on one side of the first articulation and the holes being situated on the part of the branches situated on the other side of the first articulation, the pin or pins and the hole or holes being disposed on the branch or branches so that, when the part of the arch carrying the second strut is folded over the clamp, the pin or pins each enter one of the holes. For good stability, it is preferable for each branch of the arch to be provided with two pins and as many holes as there are articulations.

In order to hold the locking means in the locking position, it is preferable to pass the second strut behind the first. For this purpose, it is possible to provide each branch of the arch with a hinge, this hinge being placed closer to the compression element than the articulation or articulations. In addition, the distance separating the notional axis passing through the two hinges from the first strut is greater than or equal to the distance separating the notional axis passing through the two hinges and the projecting end of the compression element.

In order to improve the comfort of the bracelet, it is preferable for the ends of the branches of the clamp opposite to the first strut to be provided with a boss. These bosses enable the clamp to bear on the external face of the arm opposite to the puncture point.

For a better spring effect on the one hand and better comfort on the other hand, the first strut and the branches of the clamp are curved so that the clamp has a roughly C shape. Likewise, it is preferable for the second strut also to be curved so that, when the second strut is folded over the clamp, the first strut and the second strut are curved in opposite directions.

Figure 2B:
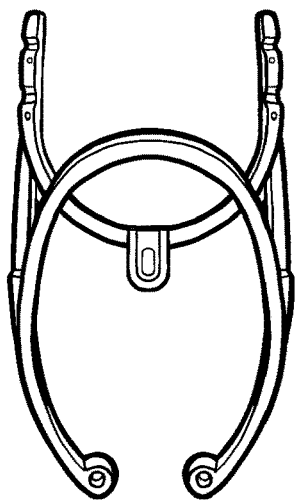
Figure 2C:
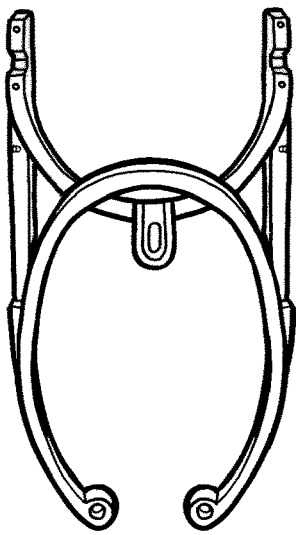
Figure 3A:
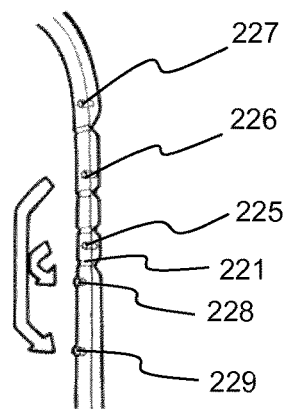
Figure 3B:
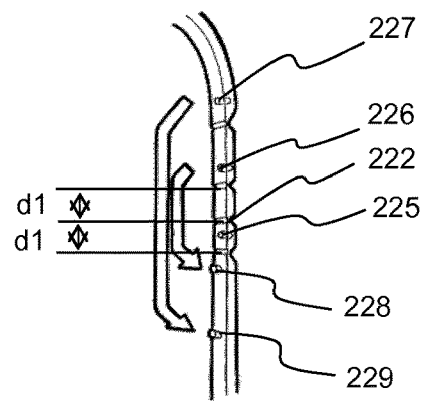
Figure 3C:
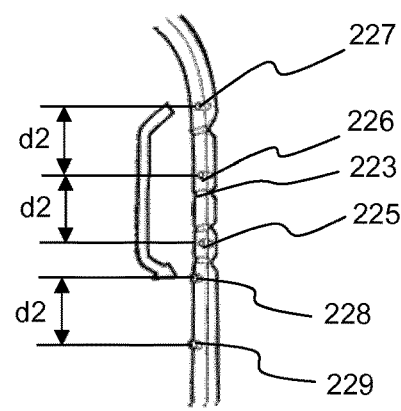
Figure 4A:
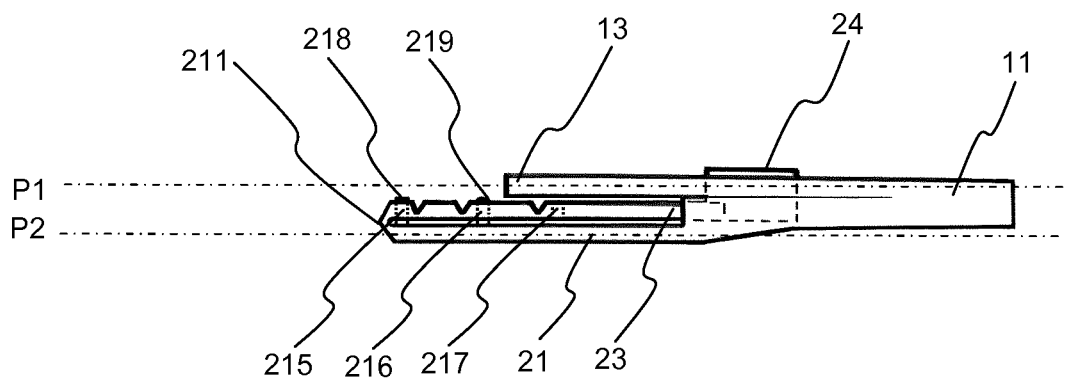
Figure 4B:
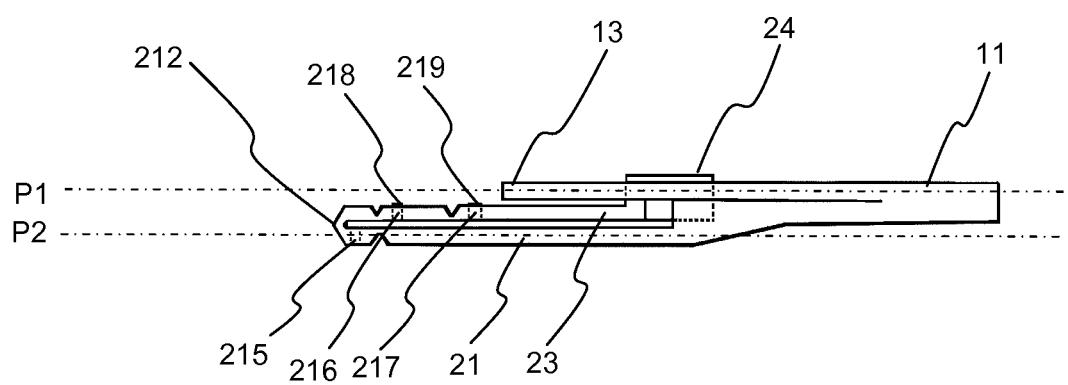
Figure 4C:
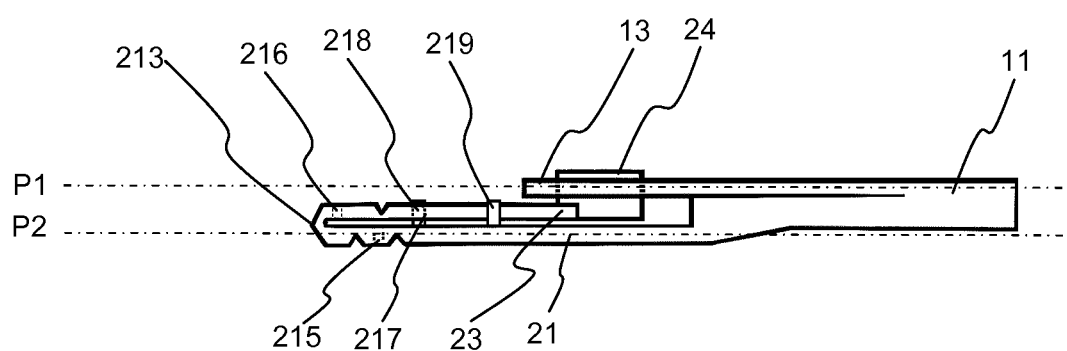
Figure 6A:
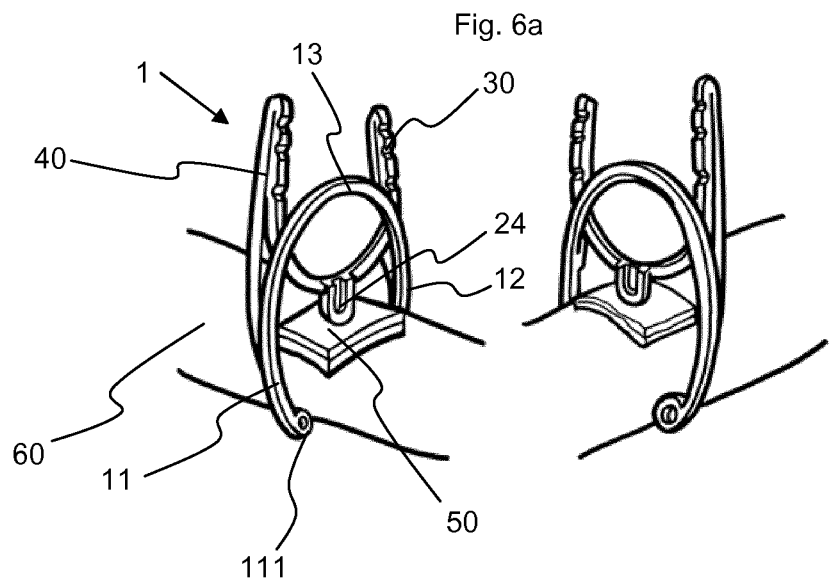
Figure 6B:
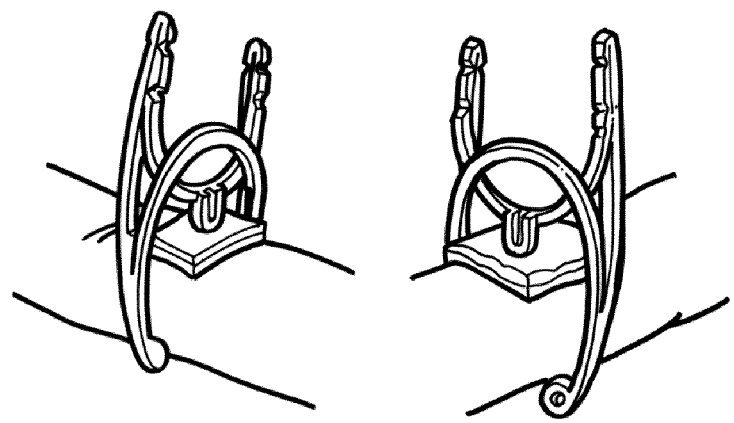
Figure 6C:
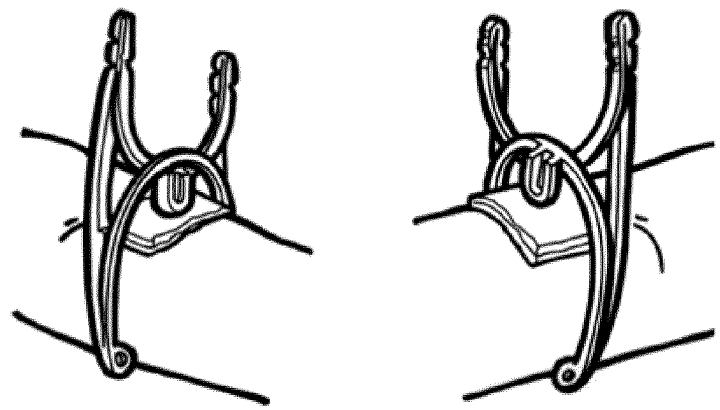
Figure 7A:
Figure 7B:
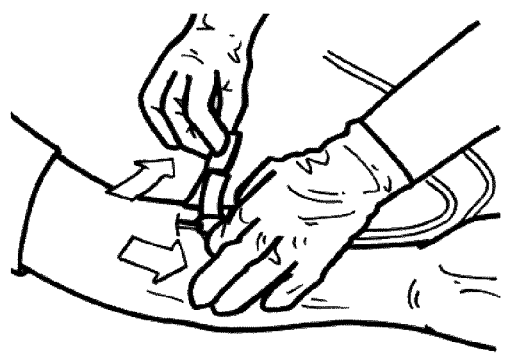
Figure 7C:
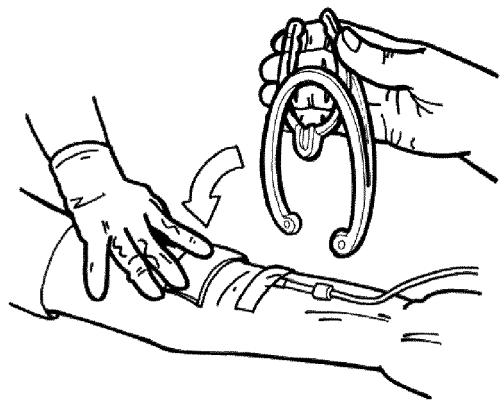
Figure 7D:
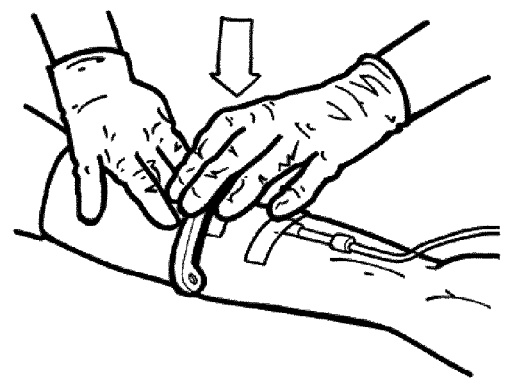
Figure 7E:
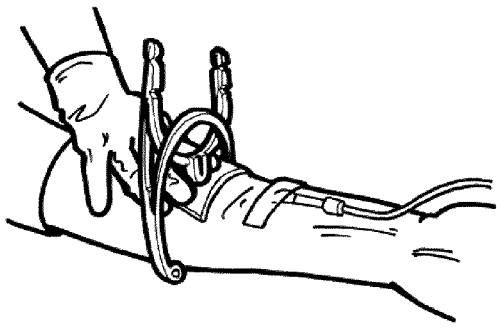
Figure 7F:
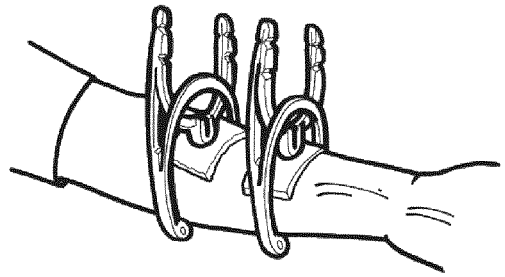

The invention is described in more detail below with the help of the figures, which show:

FIG. 1 the bracelet of the invention in the initial position (a) seen in front view and (b) seen from the back;

FIG. 2 the bracelet of FIG. 1 in the position ready for use (a) for a small-diameter arm, (b) for a medium-diameter arm and (c) for a large-diameter arm;

FIG. 3 the choice of the pins and holes according to the size of the arm (a) for a small-diameter arm, (b) for a medium-diameter arm and (c) for a large-diameter arm;

FIG. 4 the bracelet of FIG. 1 seen from the side in the position ready for use (a) for a small-diameter arm, (b) for a medium-diameter arm and (c) for a large-diameter arm;

FIG. 5 how to open the bracelet in the example of a bracelet prepared for a medium-diameter arm (a) in the idle position and (b) in the open position;

FIG. 6 the bracelet of FIG. 1 positioned on an arm, seen from the right and the left, said bracelet being placed on an arm (a) with a small diameter, (b) with a medium diameter and (c) with a large diameter;

FIG. 7 the various steps for placing the bracelet of the invention, with the example of a bracelet prepared for a medium-diameter arm.

The bracelet (1) of the invention is composed essentially of a clamp (10) intended to be placed around the arm of the patient and an arch (20) making it possible to reduce the space available in the clamp to a greater or lesser extent. It is initially flat, as manufactured (cf. FIG. 1) and must be folded in order to adopt its use form (cf. for example FIG. 2). In the first part of the description of the clamp, the relative positions of the various elements relate to the bracelet in its flat position. The bracelet is symmetrical with respect to a mirror notionally dividing the clamp and arch in two.

The clamp (10) has two symmetrical branches (11, 12) connected by a first strut preferably having the form of a first curved element (13). The branches (11, 12) are themselves curved so that the clamp has a roughly C shape. At their free end opposite to the curved element (13), each branch (11, 12) terminates in a boss (111, 121) having for example a cylindrical shape. In the present example, the bosses (111, 121) touch each other when the bracelet is in its initial position. This clamp is sized so as to be able to be placed on the arm of a patient, surrounding it at least partially. It is preferable for the thickness of the branches to be greater than that of the curved element so that the branches (11, 12) are more rigid than the first curved element (13). Thus, when the clamp is placed on the arm of the patient, the curved element by itself provides practically all the spring effect returning the branches in the direction of each other.

The arch (20) comprises two symmetrical branches (21, 22) connected together by a second strut preferably in the form of a second curved element (23). Each of the branches (21, 22) of the arch (20) is fixed to one of the branches (11, 12) of the clamp by its end opposite to the second curved element (23). The arch (20) is fixed to the clamp (10) so that, in the initial position, the first curved element (13) is placed between the second curved element (23) and the free ends of the branches (11, 12) of the clamp. The branches (21, 22) of the arch are preferably slightly more spread than the branches (11, 12) of the clamp at their junction. In the example presented here, the distance, at the junction, between the internal edges of the branches of the arch corresponds substantially to the distance between the external edges of the branches of the clamp. The branches (21, 22) of the arch are straight and parallel to each other, at least over part of their length.

In the initial state, the clamp (10) extends in a first plane (P1) and the arch (20) in a second plane (P2) substantially parallel to the first, but offset with respect to it. By convention, "front face" of the bracelet means the face in which the plane (P1) of the clamp is above the plane (P2) of the arch and "rear face" the one in which it is the plane of the arch that is above that of the clamp. Thus FIG. 1a shows the front face of the clamp and FIG. 1b the rear face.

At the top of the second curved element (23) there is a compression element (24) that diverges from the curved element in the opposite direction to the first curved element (13) when the bracelet is flat. The compression element is rounded at its end. The thickness of the compression element is preferably greater than the mean thickness of the arch so that it projects at least on one side of the arch, preferably at least on the rear face.

Each branch (21, 22) of the arch is provided with a first articulation (211; 221) and two supplementary articulations (212, 213; 222, 223). These articulations are produced for example by considerably reducing the thickness of the branches at these points so that in each case what is usually called a film hinge is formed. The distance (d1) separating the first articulations (211; 221) from the first supplementary articulations (212; 222) is equal to the distance separating the first supplementary articulations (212; 222) from the second supplementary articulations (213; 223).

Each branch of the arch is provided on its front face with three holes (215, 216, 217; 225, 226, 227) and two pins (218, 219; 228, 229) sized so as to be able to enter the holes and to be held therein by friction. The holes (215, 216, 217; 225, 226, 227) may be blind or through as is the case here. The distance (d2) separating two successive holes is equal to the distance separating the two pins. On each of the branches (21, 22) the two pins (218, 219; 228, 229) are aligned and placed between the junction with the clamp and the first articulation (211, 221). The first hole (215; 225) is placed between the first articulation (211; 221) and the first supplementary articulation (212; 222), the second hole (216, 226) beyond the second supplementary articulation (213; 223). The third hole (217, 227) is placed beyond the second hole, even further away from the first hole than the second.

Because of the symmetry of the mirror, the articulations (211, 212, 213), the holes (215, 216, 217) and the pins (218, 219) of the first branch (21) are symmetrical with the articulations (221, 222, 223), the holes (225, 226, 227) and the pins (228, 229) of the second branch (22). On the same branch, the holes and pins are substantially aligned. The three articulations of the two branches form in pairs three sets of articulations (211, 221; 212, 222; 213, 223).

In order to be used, the bracelet must be folded on itself at one of the three sets of articulations (211, 221; 212, 222; 213, 223) so as to place the compression element (24) inside the clamp (10), more or less distant from the first curved element (13). In the present example, the curved element (23) of the arch is folded towards the front face of the clamp. If the arch is folded at the first set of articulations (211, 221), that is to say at the articulations closest to the junction with the clamp, the length of the section of the branches that is situated between the first articulation and the curved element (23) is the longest. Consequently, in the folded state, the curved element (23) with the compression element (24) enters further into the clamp in the direction of the opening between the two bosses (111, 121). This position is referred to as the "small size" configuration and is depicted in particular in FIG. 2a. If the arch is folded at the first set of supplementary articulations (212, 222), the length of the section of the branches leading to the curved element (23) is shorter, so that, in the folded state, the curved element (23) with the compression element (24) does not enter as deeply into the clamp. This is the "medium size" configuration depicted in particular in FIG. 2b. Finally, if the folding is done at the second set of supplementary articulations (213, 223), the second curved element (23) and the compression element (24) scarcely enter the clamp. This is the "large size" configuration depicted in FIG. 2c. It can be seen in FIG. 2 that, the more the compression element (24) enters the clamp, the less space is available for the arm. Likewise, it can be seen that, in the folded state of the second curved element (23), the compression element (24) extends in the direction of the opening between the two bosses (111, 121), and therefore in the direction of the puncture point.

In order to hold the arch in the chosen position, the pins (218, 219; 228, 229) are introduced into the corresponding holes (215, 216, 217; 225, 226, 227). The choice of the holes is illustrated in FIG. 3. For the small-size configuration, the first pins (218, 228) enter the first holes (215, 225) and the second pins (219, 229) enter the second holes (216, 226). For the medium-size configuration, the first pins (218, 228) enter the second holes (216, 226) and the second pins (219, 229) enter the third holes (217, 227). Finally, for the large-size configuration, the first pins (218, 228) enter the third holes (217, 227), the second pins (219, 229) remaining free because of the curvature of the second curved element (23). If the position of the holes and pins with respect to the articulations were different, it could be necessary to provide fourth holes in order to allow the second pins to enter therein in the large-size position if these pins were to be placed facing the branches (21, 22).

Because of the folding of the second curved element against the clamp, either on its front face, or on its rear face after having passed behind the first curved element (13), it may happen that the compression element (24) is not situated in the space defined by the branches and the curved element of the clamp, but slightly above or below. In all cases, it is situated in the projection of this space. However, if the compression element (24) protrudes over the thickness of the second curved element (23), it may be at least partly in the space of the clamp.

To prevent the folded arch unfolding despite the interaction of the pins and holes, it is preferable to pass the curved element (23) carrying the compression element (24) behind the first curved element (13) so that it is placed between the branches (21, 22) of the arch situated in the plane P2 and the first curved element (13) of the clamp situated in the plane P1. The section of the arch carrying the compression element (24) and situated between the articulations used is therefore practically in contact with the part of the arch situated between the articulations used and the junctions with the clamp (10). This is the reason why it is preferable, at the junction between the clamp and the arch, for the rear face of the clamp to be distant from the front face of the arch by at least the thickness of the arch. To facilitate the passage of the second curved part (23) carrying the compression element behind the first curved part (13), it is preferable to provide a hinge (214; 224) on each of the branches (21, 22) for making the second curved element (23) pivot about these hinges (214, 224) while passing the compression element (24) at a distance from the first curved element (13). In other words, the distance between the axis passing through the hinges (214, 224) and the top of the first curved element is at least greater than the distance between the axis passing through the hinges (214, 224) and the projecting top of the compression element (24). The second curved element (23) is then lowered in the direction of the free ends of the clamp, passing behind the first curved element (13). For this purpose, the branches fold around at least two of the sets of articulations or the set of hinges.

The dimensions of the bracelet are chosen for example so that the usable diameter is approximately 50 mm in the small-size configuration, approximately 75 mm in the medium size and 100 mm in the large size.

In the position of use, the branches (21, 22) of the arch folded around the chosen articulations constitute actuation elements (30, 40) for spreading the branches (11, 12) of the clamp upon positioning of the bracelet. By pressing on these actuation elements so that their ends situated at the held articulations move closer together, the branches (11, 12) of the clamp are spread and the opening between the two bosses (111, 121) increases. This is clearly visible in FIG. 5.

Once the bracelet is fitted, the compression element (24) presses a compress (50) placed on the puncture point, in general on the internal face of the arm (60). The bosses (111, 121) are placed on the edges of the external face of the arm, spaced from each other to a greater or lesser extent according to the diameter of the arm. Thus, in the same size category, for example the category of medium-size arms, the bracelet in the medium-size configuration can adapt to the various diameters of this category while exerting always substantially the same pressure on the puncture point. FIG. 6 shows the bracelet of the invention in the various configurations placed on arms of different sizes. The bracelet of the invention has the advantage of not surrounding the whole of an arm as bracelets consisting of a strap do. The blood circulation is not hindered by the bracelet of the invention.

The procedure for fitting the haemostatic bracelet of the invention is illustrated in FIG. 7. First of all, the bracelet is put in the required configuration according to the diameter of the arm of the patient. After putting on protective gloves (FIG. 7a), the caregiver detaches the sticking plaster holding the needle (FIG. 7b) and then places a compress at the puncture point while pressing with the index and middle fingers on either side of the needle before withdrawing the needle (FIG. 7c). Next he opens the clamp (10) while pressing on the actuation elements (30, 40). He advances the clamp wide open while passing the bosses (111, 121) on either side of the arm and bringing the compression element (24) onto the puncture point, between the index finger and the middle finger (FIG. 7*d*). He presses firmly on the bracelet before releasing the actuation elements (FIG. 7*e*). The clamp closes again on the arm of the patient. He can now remove his fingers. In the case of haemodialyses, two needles are used. After having placed a first bracelet, the caregiver can place the second at the second puncture point (FIG. 7*f*).

Upon fitting, it is the compression element (24) that first comes into contact with the arm. It is therefore easy to apply it properly to the puncture point. The actuation elements (30, 40) are then released and the bosses (111, 121) come to bear at the same time on the external face of the arm. In addition, the two fingers of the caregiver are still surrounding the compression element at the moment when the clamp closes again. There is therefore no risk that the contact point of the compression element will move during the closure of the clamp. It should be noted that, in order to achieve this objective, it is not necessary for the bracelet to be able to adopt a plurality of different configurations. A person skilled in the art would understand that a simple bracelet consisting of a clamp (10), a compression element placed inside the clamp, projecting in the direction of the opening situated between the free ends of the branches of the clamp, and two actuation elements (30, 40) would suffice, even if it means providing the bracelet in a plurality of sizes.

By virtue of the three positions of the second curved element with respect to the first curved element, it is possible with a single bracelet to obtain three usable diameters for the clamp (10). In the same size category, the bracelet will exert substantially the same pressure, whether the arm is at one end or the other of the range of sizes recommended for this configuration.

The bracelet is maintained in the chosen configuration by virtue of the holes and pins. It goes without saying that just one pin per branch would have been able to be sufficient, although two represent a favoured solution. In addition, a person skilled in the art understands that other locking methods may be envisaged, such as for example racks on the internal or external edges of the branches of the arch and one or more indexes on the complementary part. Sleeves that can be fitted on the folded branches could also fulfil the function of locking means.

The bracelet presented here can be folded in three different sizes. It goes without saying that it would be possible choose only two sizes, or on the other hand more than three, three sizes being a good compromise.

The dimensions and the material are chosen so as to obtain preferably a compression of approximately 5 N+/−1. The material would preferably be able to be sterilised, in particular with ethylene oxide. Among all the materials that can be envisaged, polypropylene is a well suited biocompatible material.

LIST OF REFERENCES

1 Haemostatic bracelet
10 Clamp
11 First branch
111 First boss
12 Second branch
121 Second boss
13 First strut (first curved element)
20 Arch
21 First branch
211 First articulation
212 Second articulation
213 Third articulation
214 Hinge
215 First hole
216 Second hole
217 Third hole
218 First pin
219 Second pin
22 Second branch
221 First articulation
222 Second articulation
223 Third articulation
224 Hinge
225 First hole
226 Second hole
227 Third hole
228 First pin
229 Second pin
23 Second strut (second curved element)
24 Compression element
30 Actuation element
40 Actuation element
50 Compress
60 Arm
P1 Plane of the clamp
P2 Plane of the arch
d1 Distance between two articulations
d2 Distance between the pins and between the holes

The invention claimed is:

1. A haemostatic bracelet comprising:
a clamp comprising two clamp branches and a first strut, each of the clamp branches having a first end and a second end opposite to the first end, the first ends of the clamp branches being connected to one another by the first strut,
a compression element configured to be placed inside a space defined by the clamp branches and the first strut of the clamp or inside a projection of the space, the compression element protruding in a direction of an opening between the second ends of the clamp branches opposite to the first strut,
actuation elements fixed to the clamp branches so that the second ends of the clamp branches opposite to the first strut can be spread by moving ends of the actuation elements towards each other, and
an arch provided with two arch branches and a second strut,
wherein each of the arch branches has a first end and a second end opposite to the first end, the first ends of the arch branches being connected to one another by the second strut and the second ends of the clamp branches being connected respectively to a different one of the clamp branches so that, at a junction between the arch and the clamp, the arch branches diverge from the clamp in a direction away from the second ends of the clamp branches opposite to the first strut,
wherein each of the arch branches is provided with a first articulation, the first articulations of the arch branches being situated to face each other and form a first set of articulations, and
wherein the compression element is connected to the second strut so as to protrude from the second strut in a direction opposite to the first articulations of the first set of articulations.

2. The haemostatic bracelet according to claim 1, wherein a portion of the arch situated between the first articulations of the first set of articulations and comprising the second strut can be folded in a direction of the clamp by pivoting about the first articulations so that the compression element can be placed inside the space defined by the clamp branches and the first strut or inside a projection of the space while protruding in a direction of the opening between the second ends of the clamp branches opposite to the first strut.

3. The haemostatic bracelet according to claim 2, wherein retaining means are provided in order to maintain in position the portion of the arch folded against the clamp.

4. The haemostatic bracelet according to claim 3, wherein at least one of the arch branches is provided with at least one pin and one hole or at least as many holes as it has articulations, the hole or each of the holes being sized so as to receive and retain by friction the pin or one of the pins, the pin or each of the pins being placed on a first portion of the arch branch or branches situated on a first side of the first articulation and the hole or each of the holes being situated on a second portion of the arch branches situated on a second side of the first articulation opposite to the first side, the pin or pins and the hole or holes being disposed on the arch branch or branches so that, when the portion of the arch carrying the second strut is folded over the clamp, the pin or each of the pins enters the hole or a respective one of the holes, the pin or pins and the hole or holes being the retaining means.

5. The haemostatic bracelet according to claim 4, wherein each of the arch branches is provided with two pins and as many holes as there are articulations.

6. The haemostatic bracelet according to claim 1,
wherein each of the arch branches is provided with one or more supplementary articulations, each of the supplementary articulations of a first one of the clamp branches facing a corresponding one of the supplementary articulations of a second one of the clamp branches and forming with this corresponding articulation a set of supplementary articulations,
wherein a portion of the arch comprising the second strut can be folded in the direction of the clamp by pivoting as required about the first set of articulations or one of the set or sets of supplementary articulations, and
wherein the set or sets of supplementary articulations are further away from the junction between the arch and the clamp than the first set of articulations, so that, in the folded position of the second strut on the clamp, the compression element is closer to the opening situated between the second ends of the clamp branches opposite to the first strut, when the second strut has pivoted about the first set of articulations, than when the second strut has pivoted about one of the set or sets of supplementary articulations.

7. The haemostatic bracelet according to claim 6, wherein each of the arch branches comprises a first supplementary articulation and a second supplementary articulation forming a first set of supplementary articulations and a second set of supplementary articulations, the first set of supplementary articulations being further away from the junction between the arch and the clamp than the first set of articulations and the second set of supplementary articulations being further away from the junction between the arch and the clamp than the first set of supplementary articulations.

8. The haemostatic bracelet according to claim 7, wherein retaining means are provided in order to maintain in position the portion of the arch folded against the clamp.

9. The haemostatic bracelet according to claim 8, wherein at least one of the arch branches is provided with at least one pin and one hole or at least as many holes as it has articulations, the hole or each of the holes being sized so as to receive and retain by friction the pin or one of the pins, the pin or each of the pins being placed on a first portion of the arch branch or branches situated on a first side of the first articulation and the hole or each of the holes being situated on a second portion of the arch branches situated on a second side of the first articulation opposite to the first side, the pin or pins and the hole or holes being disposed on the arch branch or branches so that, when the portion of the arch carrying the second strut is folded over the clamp, the pin or each of the pins enters the hole or a respective one of the holes, the pin or pins and the hole or holes being the retaining means.

10. The haemostatic bracelet according to claim 9, wherein each of the arch branches is provided with two pins and as many holes as there are articulations.

11. The haemostatic bracelet according to claim 6, wherein retaining means are provided in order to maintain in position the portion of the arch folded against the clamp.

12. The haemostatic bracelet according to claim 11, wherein at least one of the arch branches is provided with at least one pin and one hole or at least as many holes as it has articulations, the hole or each of the holes being sized so as to receive and retain by friction the pin or one of the pins, the pin or each of the pins being placed on a first portion of the arch branch or branches situated on a first side of the first articulation and the hole or each of the holes being situated on a second portion of the arch branches situated on a second side of the first articulation opposite to the first side, the pin or pins and the hole or holes being disposed on the arch branch or branches so that, when the portion of the arch carrying the second strut is folded over the clamp, the pin or each of the pins enters the hole or a respective one of the holes, the pin or pins and the hole or holes being the retaining means.

13. The haemostatic bracelet according to claim 12, wherein each of the arch branches is provided with two pins and as many holes as there are articulations.

14. The haemostatic bracelet according to claim 6, wherein each of the arch branches is provided with a hinge, the hinge being placed closer to the compression element than the articulation or articulations, and
wherein a distance separating the first strut from a notional axis passing through the hinges is greater than or equal to a distance separating a protruding end of the compression element from the notional axis passing through the hinges.

15. The haemostatic bracelet according to claim 1, wherein each of the arch branches is provided with a hinge, the hinge being placed closer to the compression element than the articulation or articulations, and
wherein a distance separating the first strut from a notional axis passing through the hinges is greater than or equal to a distance separating a protruding end of the compression element from the notional axis passing through the hinges.

16. The haemostatic bracelet according to claim 1, wherein the second ends of the clamp branches opposite to the first strut are provided with a boss.

17. The haemostatic bracelet according to claim 1, wherein the first strut and the clamp branches are curved so that the clamp has a roughly C shape.

18. The haemostatic bracelet according to claim 1, wherein the first strut and the clamp branches are curved so that the clamp has a roughly C shape, and wherein the second strut is curved so that, when the second strut is folded over the clamp, the first strut and the second strut are curved in opposite directions.

* * * * *